United States Patent
Chi et al.

(10) Patent No.: US 9,314,183 B2
(45) Date of Patent: Apr. 19, 2016

(54) TRANSDUCER ASSEMBLIES FOR DRY APPLICATIONS OF TRANSDUCERS

(71) Applicants: Yu Mike Chi, San Diego, CA (US); Michael Henry Elconin, El Cajon, CA (US); Trevor Austin Kerth, San Diego, CA (US)

(72) Inventors: Yu Mike Chi, San Diego, CA (US); Michael Henry Elconin, El Cajon, CA (US); Trevor Austin Kerth, San Diego, CA (US)

(73) Assignee: Cognionics, Inc., San Diego, CA (US)

( * ) Notice: Subject to any disclaimer, the term of this patent is extended or adjusted under 35 U.S.C. 154(b) by 0 days.

(21) Appl. No.: 13/982,724

(22) PCT Filed: Mar. 15, 2013

(86) PCT No.: PCT/US2013/032015
§ 371 (c)(1),
(2) Date: Jul. 30, 2013

(87) PCT Pub. No.: WO2013/142316
PCT Pub. Date: Sep. 26, 2013

(65) Prior Publication Data
US 2015/0141788 A1 May 21, 2015

Related U.S. Application Data

(60) Provisional application No. 61/612,867, filed on Mar. 19, 2012, provisional application No. 61/652,073, filed on May 25, 2012.

(51) Int. Cl.
*A61B 5/0478* (2006.01)
*A61B 5/00* (2006.01)

(52) U.S. Cl.
CPC .......... *A61B 5/0478* (2013.01); *A61B 5/6803* (2013.01)

(58) Field of Classification Search
CPC ..................................... A61B 5/0478
USPC .......................... 600/383; 607/139
See application file for complete search history.

(56) References Cited

U.S. PATENT DOCUMENTS

| 2,426,958 | A | * | 9/1947 | Ulett, Jr. et al. ............... 600/383 |
| 4,967,038 | A | | 10/1990 | Gevins et al. |
| 5,038,782 | A | * | 8/1991 | Gevins et al. ................. 600/383 |
| 6,201,982 | B1 | * | 3/2001 | Menkes et al. ............... 600/386 |
| 8,392,250 | B2 | * | 3/2013 | Pradeep et al. ............ 705/14.41 |
| 8,548,554 | B2 | * | 10/2013 | Popescu et al. ............... 600/383 |
| 2009/0134887 | A1 | | 5/2009 | Hu et al. |

FOREIGN PATENT DOCUMENTS

EP 2417904 A2 2/2012

* cited by examiner

*Primary Examiner* — Lee S Cohen
(74) *Attorney, Agent, or Firm* — Edward W. Callan

(57) ABSTRACT

A transducer assembly including a support terminal and at least one probe extending from the support terminal is adapted to enable a transducer to penetrate and slide through patches of hair covering a subject area of a person. The probe includes at least one leg structure supporting a transducer disposed at the distal end of the leg structure for sensing or stimulating the state of a particular property of a selected subject area when the transducer is applied by the leg structure to the selected subject area. The leg structure is so disposed in relation to the support terminal as to be disposed at a non-perpendicular angle to the subject area when the transducer assembly is applied to the selected subject area. The leg structure is adapted to flex when the transducer is applied under pressure to the selected subject area to thereby cause the transducer to slide on the subject area.

16 Claims, 5 Drawing Sheets

TRANSDUCER ASSEMBLIES FOR DRY APPLICATIONS OF TRANSDUCERS

CROSS-REFERENCE TO RELATED APPLICATIONS

This application claims benefit of U.S. Provisional Patent Application No. 61/612,867 filed Mar. 19, 2012 and U.S. Provisional Patent Application No. 61/652,073 filed May 25, 2012.

BACKGROUND OF THE INVENTION

The present invention generally pertains to transducer assemblies, such as a sensor assembly that enables communication to an external device from a transducer, and is particularly directed to the application of a sensing transducer to a subject area. As used herein the term "subject area" means the scalp, the chest or any other region of a human body. The state of a particular property of the selected subject area, such as bioelectrical potential, that is sensed by the transducer is communicated by the transducer assembly to an external device.

For EEG (electroencephalograph) applications, in which the sensing transducers are electrodes, sensor assemblies are used to apply electrodes to a subject area to enable the sensing of bioelectric potentials. For some subject areas, sensor assemblies that include so-called wet electrodes, which adhere to the body, are preferred. Conventional wet-electrode sensor assemblies include an Ag/AgCl disc (or a disc of some other conductive material). A wet conductive gel is used to establish an electrical connection through any hair between the subject area and the Ag/AgCl disc. Electrical potentials on the surface of the subject area are coupled via the gel to the Ag/AgCl disc and into an electronic amplifier. A standard wet electrode sensor assembly provides a secure, low-impedance electrical connection between the subject area and a recording instrument, and thereby ensures high quality signal sensing. However, the use of electrolytic gels in combination with the need for skin preparation is often time consuming for the user to set up, and irritating and uncomfortable for the subject. Alternatively, dry electrodes, which are designed to push through the hair to directly contact the scalp and do not require conductive gels or scalp preparation, have been explored as alternatives to wet electrodes.

In practice, dry electrodes suffer from numerous usability issues. Although acquiring signals on bare skin (e.g., forehead) is relatively straightforward, most EEG setups also require electrodes on areas of the head covered by hair. Patches of hair, depending on thickness, are often difficult to reliably penetrate and they block the sensor from physically reaching the skin. The presence of hair has made it challenging to build a dry EEG system that can be easily and rapidly donned by a subject with minimal assistance or adjustment.

Known prior art dry EEG electrodes typically utilize straight, hard fingers that are designed to push through strands of hair to the scalp. Although finger electrodes can be effective at reaching the scalp through many different hair types, they have several drawbacks. If the diameter of the finger is small enough to easily penetrate between hairs, it can become painful due to the high stress concentration where the sharp points contact the scalp. Larger diameter fingers that do not cause discomfort on the head often cannot penetrate between hairs without manual adjustment. Straight-finger electrodes, when made out of a hard material, are also an injury hazard under impact conditions. Examples of prior art dry electrodes are described in U.S. Pat. No. 4,967,038 and United States Patent Application Publication No. 2009/0030298 A1, and on the website of g.tec medical engineering under the heading: "g.SAHARA ACTIVE DRY EEG ELECTRODE SYSTEM".

Both wet electrodes and dry electrodes require some pressure application mechanism to physically secure them to the subject's head. For wet electrodes, the holding mechanism can be an adhesive, wherein the electrode is glued to the scalp. For dry electrodes, the holding mechanism includes elastic caps and mechanical headgear apparatus in the absence of an adhesive.

SUMMARY OF THE INVENTION

The present invention provides a transducer assembly, comprising: a support terminal; and at least one probe attached to and extending from the support terminal; wherein the at least one probe includes at least one leg structure supporting a transducer disposed at the distal end of the leg structure for sensing or stimulating the state of a particular property of a selected subject area when the transducer is applied by the leg structure to the selected subject area; and wherein the at least one leg structure is so disposed in relation to the support terminal as to be disposed at a non-perpendicular angle to the subject area when the transducer assembly is applied to the selected subject area.

In some embodiments, the at least one leg structure is adapted to flex when the transducer is applied under pressure to the selected subject area to thereby cause the transducer to slide on the subject area.

The flex-and-slide feature of the transducer assembly of the present invention is discussed below following the descriptions of the illustrated exemplary embodiments.

The transducer assembly of the present invention enables a transducer to penetrate and slide through patches of hair covering a subject area, while remaining comfortable and safe. The risk of discomfort and injury is minimized since any applied pressure causes the leg supported transducer to slide on the surface of the body, rather than into the body. The sliding action also helps part hair and positions the transducer underneath the hair and directly on the skin. Under high pressure or impact, the flexible leg can be configured to collapse until it is flattened with the entire electrode assembly, which thereby further decreases the possibility of injury.

Preferably, more than one probe is attached to the support electrode for mechanical stability.

Transducers that may be used with the transducer assembly of the present invention include, but are not limited to, transducers that sense electrical characteristics, temperature, and optical properties and transducers that are used to deliver an electrical current for transcranial stimulation.

In some embodiments, a plurality of transducer assemblies according to the present invention are so combined with a cap, strap or harness as to apply their respective transducers to a plurality of subject areas when the cap, strap or harness is disposed to position the transducer assemblies over the plurality of subject areas.

Additional features of the present invention are described with reference to the detailed description of the preferred embodiments.

DETAILED DESCRIPTION

Figure 1:
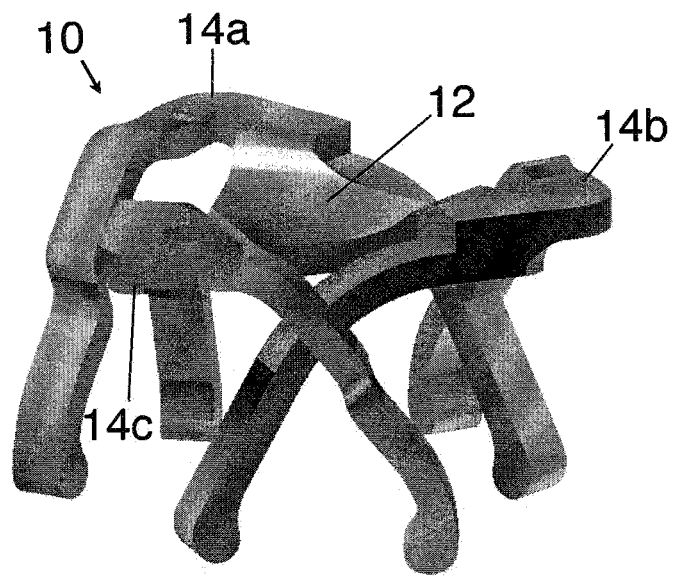
FIG. 1 is an isometric view of one embodiment of a transducer assembly according to the present invention.
Figure 2:
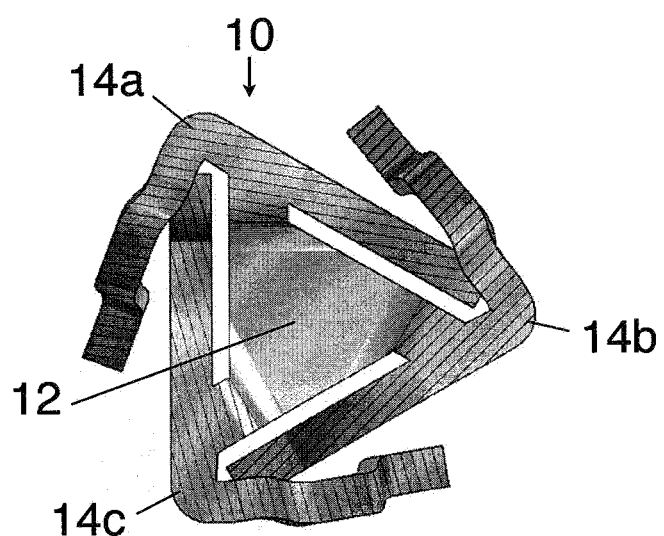
FIG. 2 is top view of the transducer assembly shown in FIG. 1.

Referring to FIGS. 1 and 2, one exemplary embodiment of a transducer assembly 10 according to the present invention includes a support electrode 12 and a plurality of probes 14a, 14b and 14c that are attached to and extend from the support electrode 12. The support electrode 12 supports the probes 14a, 14b, 14c in a triangular configuration. The support electrode 12 also serves as an attachment point for external signal connectors. Although the support electrode 12 is depicted as triangular in FIG. 1, the support electrode 12 may be of any shape. In other versions of this other embodiment, there may be more or less than six probes.

Figure 3:
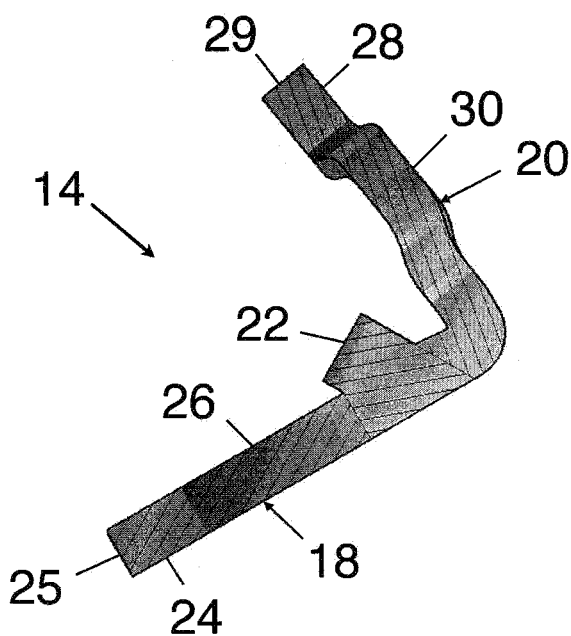
FIG. 3 is top view of a pair of probes included in the transducer assembly shown in FIGS. 1 and 2.

Referring to FIG. 3, an individual probe 14 includes a lower leg structure 18, an upper leg structure 20 and a branch 22 at which the probe 14 is connected to the support electrode 12. The lower leg structure 18 includes a foot 24, which supports a transducer 25, and a flexible joint 26. The upper leg structure 20 includes a foot 28, which supports a transducer 29, and a flexible joint 30. When the respective transducers 25, 29 are in contact with a subject area and pressure is applied to the support electrode 22, the lower and upper leg structures 18, 20 flex at their respective joints 26, 30 and cause the foot-supported transducers 25, 29 to slide on the subject area.

Figure 4:
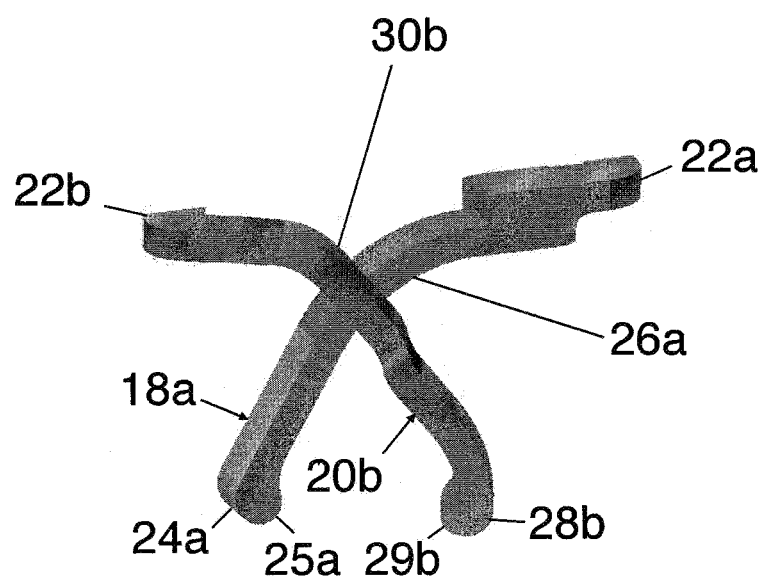
FIG. 4 illustrates a crossing disposition of upper and lower leg structures of different probes in the transducer assembly shown in FIG. 1

Although both the lower leg structure 18 and the upper leg structure 20 contain similar components, they have different shapes and are arranged in different orientations, as shown in FIGS. 1 and 4, to minimize the radial expansion of the transducer assembly 10 as each leg structure 18, 20 flexes.

Referring further to FIG. 4, which illustrates the disposition of the lower leg structure 18a of one probe 14a in relation to the upper leg structure 20b of an adjacent probe 14b, the lower leg structure 18a of the one probe 14a is disposed to cross beneath the upper leg structure 20b of the adjacent probe 14b. Such crossing is accommodated by the humped shape of the joint 30b in the upper leg structure 20. In this embodiment, the lower leg structure 18 of each probe 14a-c fits beneath the upper leg structure 20 of adjacent probe 14a-c, with the crossing adjacent leg structures 18, 20 being oriented in a somewhat tangential direction to the perimeter of the support electrode 12. This arrangement allows each lower leg structure 18 to fold beneath an upper leg structure 20 as they flex, to thereby minimize the overall area of the transducer assembly 10. Minimizing the overall area is particularly advantageous for high-density arrays of transducer assemblies 10 where multiple transducer assemblies 10 must be placed in close proximity.

Figure 5:
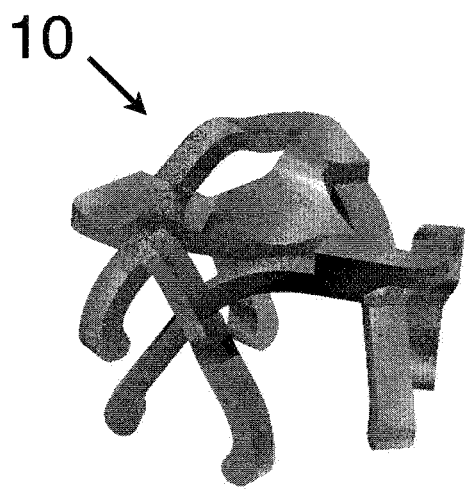
FIG. 5 illustrates the flexing of the leg structures of the transducer assembly shown in FIG. 1 when insufficient pressure is applied to the transducer assembly to compress the transducer assembly in a direction perpendicular to a subject area.
Figure 6:
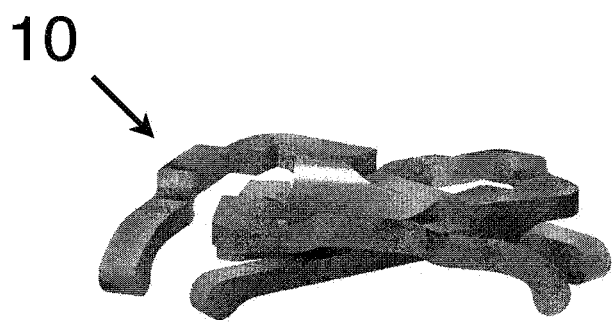
FIG. 6 illustrates the folding of the leg structures of the transducer assembly shown in FIG. 1 when sufficient pressure is applied to the transducer assembly to compress the transducer assembly in a direction perpendicular to a subject area.

To better illustrate the flexing and folding of the leg structures 18 20, FIGS. 5 and 6 illustrate the sensor assembly 10 in uncompressed and compressed states, respectively. When the sensor assembly 10 is flattened, the leg structures 18, 20 flex, with the lower leg structures 18 fitting beneath the upper leg structures 20. The flexing action causes the transducers 25, 29 to slide on the subject area. In instances where there is hair on the subject area, the sliding action helps position the transducers 25, 29 beneath the hair strands for better contact directly with skin or scalp. Since the leg structures 18, 20 within all of the probes 14a-c flatten, the present invention reduces the risk of injury to the subject, in contrast to prior art dry-electrode assemblies having straight fingers.

Figure 7:
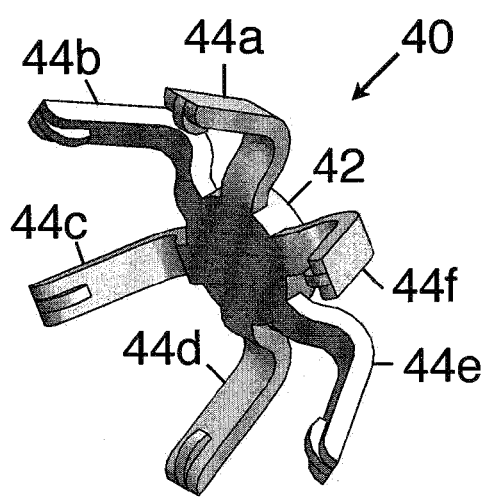
FIG. 7 is an isometric view of another embodiment of a transducer assembly according to the present invention.

Referring to FIG. 7, another exemplary embodiment of a transducer assembly 40 according to the present invention includes a support electrode 42 and six probes 44a, 44b, 44c, 44d, 44e and 44f, which are attached to and extend from the support electrode 42. The support electrode 42 supports the six probes 44a, 44b, 44c, 44d, 44e and 44f. In other versions of this other embodiment, there may be more or less than six probes. The support electrode 42 also serves as an attachment point for external signal connectors. Although the support electrode 42 is illustrated as circular in FIG. 4, the support electrode 42 may be of any shape.

Figure 8:
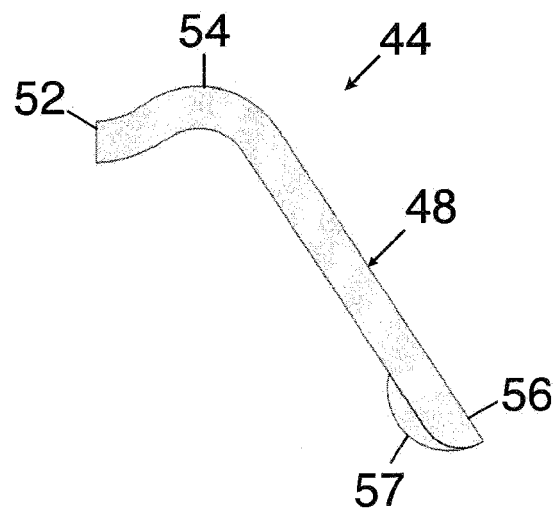
FIG. 8 is plan side view of a probe included in the transducer assembly shown in FIG. 7.
Figure 9:
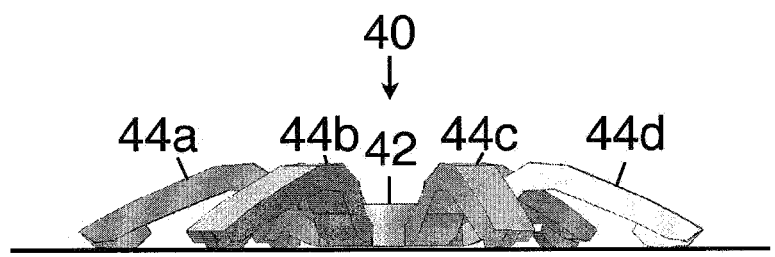
FIG. 9 illustrates the folding of the leg structures of the transducer assembly shown in FIG. 7 when high pressure is applied to the transducer assembly in a direction perpendicular to a subject area.

Referring to FIG. 8, an individual probe 44 includes only one leg structure 48. The leg structure 48 includes a branch 52, at which the probe 44 is connected to the support electrode 42, a flexible joint 54 and a foot 56, which supports a transducer 57. When the transducer 57 is in contact with a subject area and pressure is applied to the support electrode 42, the leg structure 48 flexes outward at the joint 54, and cause the foot-supported transducers 55 to slide on the subject area. In instances where there is hair on the subject area, the sliding action helps position the transducer 57 beneath the hair strands for better contact directly with skin or scalp. Since all the leg structures 48 within all of the probes 44 flatten when sufficient pressure is applied to the support electrode 42, as shown in FIG. 9, the present invention reduces the risk of injury to the subject, in contrast to prior art dry-electrode assemblies having straight fingers.

Figure 10:
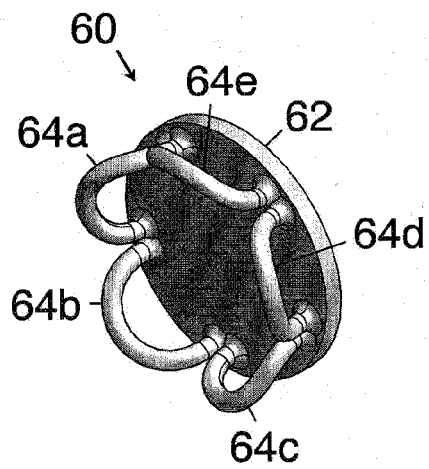
FIG. 10 is an isometric view of a further embodiment of a transducer assembly according to the present invention.

Referring to FIG. 10, a further exemplary embodiment of a transducer assembly 60 according to the present invention includes a support electrode 62 and five probes 64a, 64b, 64c, 64d and 64e, which are supported by and extend outward from the baseplate 62 in a direction that is non-perpendicular to the support electrode 62. In other versions of this other embodiment, there may be more or less than five probes.

Figure 11:
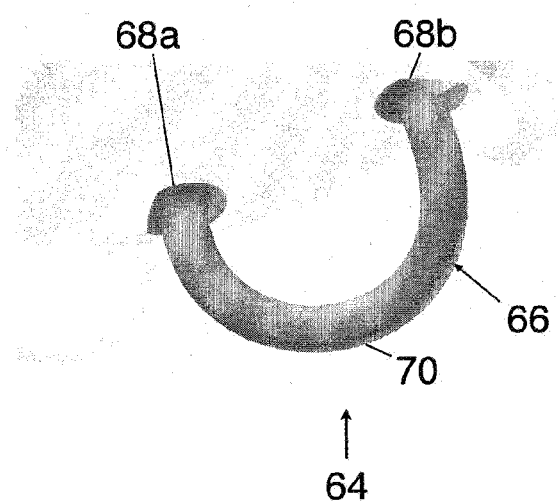
FIG. 11 is an isometric view of a probe included in the transducer assembly shown in FIG. 10.

Referring to FIG. 11, an individual probe 64 includes a single loop-shaped leg structure 66 having two terminals 68a, 68b, which are attached to the support electrode 62. At least part of the loop-shaped leg structure 66 is made of flexible material which is disposed so that leg structure 66 flexes outward from the support electrode 62 when pressure is applied to the support electrode 62. In other versions of this further embodiment, the loop-shaped leg structure 66 includes joints disposed in the regions adjacent the terminals 68a, 68b, wherein the joints enable the leg structure 66 to flex outward from the support electrode 62 when pressure is applied to the support electrode 62.

A transducer 70 is disposed at the distal end of the leg structure 66 for sensing or stimulating the state of a particular property of a selected subject area when the transducer 70 is applied by the leg structure to the selected subject area when pressure is applied to the support electrode 62 to thereby cause the transducer 70 to slide on the subject area.

One advantage of the loop shape of the leg structure 66 is that the flexing action is bettered constrained to only a radial, outward direction with respect to the support electrode 62 and thereby prevents the leg structure 66 from bending in a sub-optimal direction (e.g., sideways), which may compromise its integrity. A second advantage of the loop shape is that that the transducer 70 can be made part of the loop, which enables the transducer 70 to bend under pressure and provide greater conformity and contact area to the surface of the subject.

Figure 12:
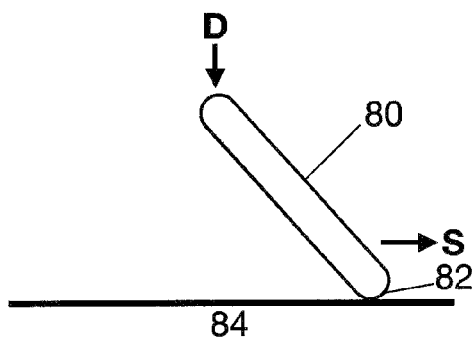
FIGS. 12 and 13 illustrate the flex-and-slide feature of the present invention.
Figure 13:
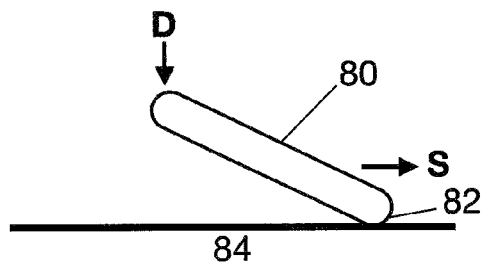

The flex-and-slide feature of the transducer assembly of the present invention is discussed with reference to FIGS. 12 and 13. A generalized probe 80 having a transducer 82 at the distal end of the probe 80 is disposed at a non-perpendicular angle to a subject area 84 while being oriented in a non-parallel direction to an applied force D. In a typical prior art EEG system, a head cap, strap or other harness system usually supplies this force D perpendicular to the subject area 84. Because the transducer assembly of the present invention orients the probe 80 in a non-perpendicular direction to the subject area 84, the force D causes the probe 80 to deflect in the direction S enabling the contact transducer 82 to slide on the subject area 84. The contact 82 is made of a conductive material to acquire electrical signals from the subject area 84. The sliding action enables the tip of the transducer 82 to push aside hair and achieve better contact to the subject area 84. Under extreme pressure the probe 80 simply flattens on its side and against the subject area 84 and thereby broadly distributes over the subject area 84. The sliding action of the current invention in combination with the ability of the probe 80 to flatten under extreme pressure enables the transducer 82 to both penetrate and push aside hair while maintaining comfort and safety.

In embodiments of the invention that utilize electrical transduction, the support electrode and the probes of the transducer assembly are capable of transferring electrical signals between the transducer and an external device. This can be accomplished by different techniques. In some embodiments, the support electrode and the probes are made from nylon or any other elastomer plastics that are flexible and bendable; and a silver paint is applied to the surface to make the support electrode and probes electrically conductive. An alternative technique involves immersing a plastic support terminal and plastic probes in an electroplating bath that coats their surfaces with electrically conductive material. Alternatively, the entire transducer assembly can be made from a conductive material such as carbon filled plastic, conductive silver-silicone compounds or solid metal. As a further alternative, since only the contact area of the transducer at the distal end of the probe needs to be conductive, only the contact area of the transducer is painted/coated or made from a conductive material; and signals are communicated to or from the transducer by a conductive wire that is embedded in or runs alongside the remainder of the transducer assembly.

In those exemplary embodiments that include a joint in the leg structure, an explicit joint is not required. The joint can simply be a flexing function provided by the leg structure being attached to the support electrode; or the flexibility function of the joint is inherent to the leg structure, such as when the leg structure is made of a sufficiently flexible material.

The transducer assembly of the present invention is broadly applicable to a variety of other embodiments that involve placing a transducer on the surface of a person in addition to embodiments that are used for sensing a bioelectric potential. In one embodiment, a thermistor is supported by the leg structures of the probes to sense head temperature through hair. Another application involves placing optical sensors at the distal ends of the leg structures for measuring blood oxygen saturation or near infrared spectroscopy. In yet another embodiment, the transducer assembly is used to deliver electrical current, rather than or in addition to sensing bioelectric potential, for transcranial stimulation.

In an exemplary embodiment of a method of using the transducer assembly of the present invention in an EEG system, the transducers are electrodes that are connected to the input of an EEG system; and multiple electrodes are disposed inside a headset cap, strap or harness to facilitate the placement of multiple channels on a subject.

Light downward pressure applied by the cap has the effect of pushing the tips of the leg structures tangentially along the subject area to push hair out of the way to enable the electrodes to make contact with the skin. In a multi-electrode configuration each electrode is typically be incorporated into a headset cap that can apply pressure to cause all the electrodes to simultaneously to slide on the respective subject areas and thereby enable rapid application of the pressure.

When the recording is finished, the user simply removes the electrode and/or the headset, strap or harness.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the exemplary embodiments described herein but rather by the claims and their legal equivalents.

The invention claimed is:

1. A transducer assembly, comprising:
    a support terminal; and
    at least one probe attached to and extending from the support terminal;
    wherein the at least one probe includes at least one leg structure supporting a dry electrode disposed at a distal end of the leg structure for sensing or stimulating the state of a particular property of a selected subject area when the dry electrode is applied by the leg structure to the selected subject area; and
    wherein the at least one leg structure is so disposed in relation to the support terminal as be disposed at a non-perpendicular angle to the subject area when the dry-electrode assembly is applied to the selected subject area; and
    wherein the at least one probe includes a plastic material that is flexible and bendable.

2. A transducer assembly according to claim 1, wherein the at least one leg structure is adapted to flex when the dry electrode is applied under pressure to the selected subject area to thereby cause the dry electrode to slide on the subject area.

3. A transducer assembly according to claim 2, wherein a plurality of said probes are attached to extend from the support terminal.

4. A transducer assembly according to claim 3, wherein individual said probes include a plurality of said leg structures.

5. A transducer assembly according to claim 4,
wherein individual said probes include an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

6. A transducer assembly according to claim 4,
wherein individual said probes include an upper leg structure and a lower leg structure; and
wherein the lower leg structure of one said probe is disposed to cross beneath the upper leg structure of an adjacent said probe to minimize the radial expansion of the transducer assembly as each said leg structure flexes.

7. A transducer assembly according to claim 3,
wherein individual said probes include an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

8. A transducer assembly according to claim 3, wherein individual said probes include a loop-shaped leg structure that extends outward from the support terminal in a direction that is non-perpendicular to the support terminal.

9. A transducer assembly according to claim 2,
wherein an individual said probe includes an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

10. A transducer assembly according to claim 1, wherein a plurality of said probes are attached to extend from the support terminal.

11. A transducer assembly according to claim 10, wherein individual said probes include a plurality of said leg structures.

12. A transducer assembly according to claim 11,
wherein individual said probes include an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

13. A transducer assembly according to claim 11,
wherein individual said probes include an upper leg structure and a lower leg structure; and
wherein the lower leg structure of one said probe is disposed to cross beneath the upper leg structure of an adjacent said probe to minimize the radial expansion of the transducer assembly as each said leg structure flexes.

14. A transducer assembly according to claim 10,
wherein individual said probes include an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

15. A transducer assembly according to claim 10, wherein individual said probes include a loop-shaped leg structure that extends outward from the support terminal in a direction that is non-perpendicular to the support terminal.

16. A transducer assembly according to claim 1,
wherein an individual said probe includes an upper leg structure and a lower leg structure; and
wherein individual said leg structures includes a foot, which supports a dry electrode, and a flexible joint so that when the respective dry electrodes are in contact with a subject area and pressure is applied to the support terminal, the upper and lower leg structures flex at their respective joints and cause the foot-supported dry electrodes to slide on the subject area.

* * * * *